United States Patent [19]

Laird

[11] Patent Number: 4,912,779

[45] Date of Patent: Apr. 3, 1990

[54] VISOR

[76] Inventor: Albert W. Laird, 652 Ridgecrest Dr., Bowling Green, Ky. 42101

[21] Appl. No.: 240,518

[22] Filed: Sep. 6, 1988

[51] Int. Cl.$^4$ .............................................. A61F 9/04
[52] U.S. Cl. ............................................. 2/12; 2/197
[58] Field of Search ...................... 2/12, 197, 200, 171, 2/DIG. 11, 177

[56] References Cited

U.S. PATENT DOCUMENTS 2,988,743  6/1961  Wagenfeld ................................. 2/12
3,271,778  9/1966  Ferguson ................................... 2/12
4,106,119  8/1978  Taupin ...................................... 2/12

Primary Examiner—Peter Nerbun
Attorney, Agent, or Firm—Anthony A. O'Brien

[57] ABSTRACT

A visor formed from sheet material includes a bill formed with integral straps, one of which has a slot near its end extending obliquely across the strap. The other strap has a series of triangular teeth on both of its edges, which provide positive locking within the slot, and yet easy adjustment of the visor for head size.

2 Claims, 1 Drawing Sheet

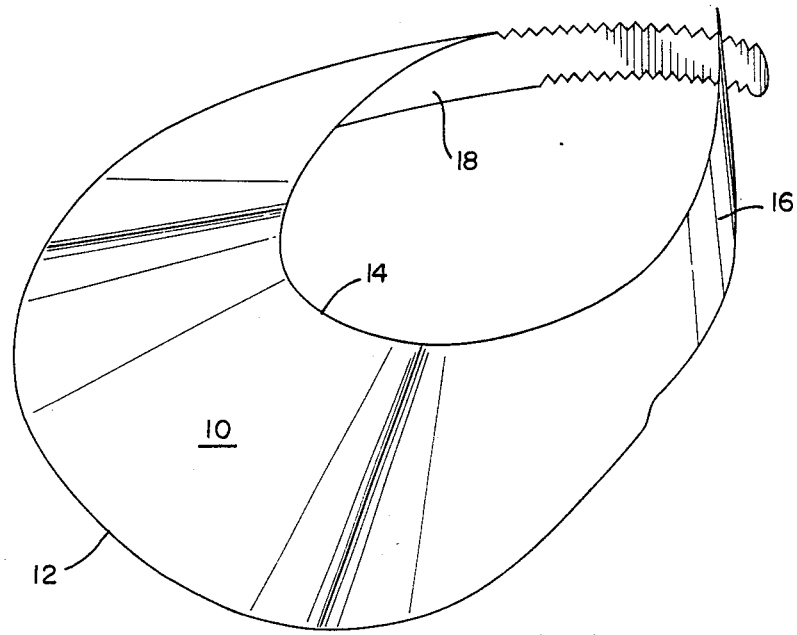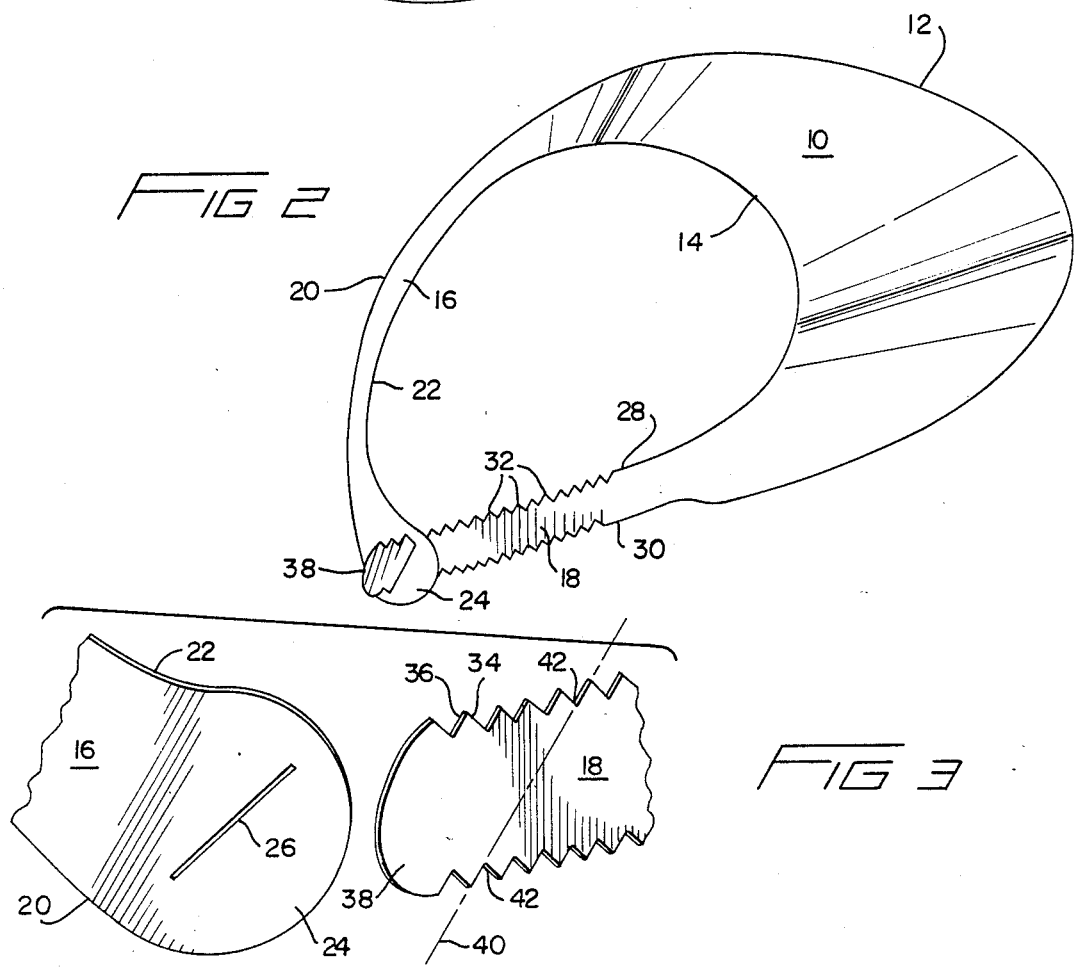

VISOR

BACKGROUND OF THE INVENTION

This invention relates to visors, sun shields, caps and the like having headbands which can be adjusted to the size of the wearer's head.

It is common to provide visors and the like with some type of headband, such as shown for example in U.S. Pat. Nos. 2,988,743 and 3,271,778. One of the problems associated with such headbands, however, is that in order to provide for substantially positive locking at at particular head size, locking mechanisms have been provided which require significant manipulation and conscious effort on the part of the wearer. Such manipulation is made all the more difficult by the fact that the headband is best adjusted while on the head, so that the mechanism must be adjusted by feed alone.

SUMMARY OF THE INVENTION

In view of the foregoing, it is an object of this invention to provide a visor having a headband whose length can be easily adjusted while the visor is on one's head.

Another object of the invention is to provide a visor with a mechanism that locks positively, and with which tension on the headband increases the locking force.

These and other objects are attained by a visor formed from sheet material, including an arcuate bill and integrally connected thereto a first strap, including a distal end having a slot extending obliquely across the strap, and a second strap bounded by serrated edges. The slot is wider than the second strap to permit insertion of the latter, and each of the serrated edges comprises a series of triangular teeth which engage the ends of the slot to provide a positive locking action.

In a preferred construction, the slot is angled obliquely across its strap in such a way that if extended, its point of intersection with the outer edge of the strap would be closer to the bill than its point of intersection with the inner edge of the strap.

BRIEF DESCRIPTION OF THE DRAWING

In the accompanying drawing, FIG. 1 is a perspective view, looking obliquely downward at the front of a visor embodying the invention;

FIG. 2 is a perspective view of the visor taken from the rear thereof; and

FIG. 3 is a detailed view of a connecting mechanism of the headband.

DESCRIPTION OF THE PREFERRED EMBODIMENT

A visor embodying the invention is cut from a stiff, resilient sheet material, preferably a paper product such as bristol board or cardboard. As shown in FIGS. 1 and 2, the visor includes a broad bill 10 defined between arcuate peripheral and interior edges 12 and 14, which draw nearer to one another at the sides of the bill, and extend therefrom generally parallel to each other to define a first strap 16 and a second strap 18 at opposite sides of the bill.

Referring to FIG. 2, the first strap 16 has an outer edge 20 and an inner edge 22, and terminates at an enlarged rounded distal end 24. A slot 26 is cut in the end 24, between but not extending to the edges 20 and 22, along a slightly oblique line that, if extended to meet the edges of the strap, would intersect the outer edge of the strap at a point closer to the bill than the point at which it would intersect the inner edge of the strap. That is, the slot inclines rearwardly in the direction of the opposite strap. A first portion of the distal end 24 is defined adjacent one end of slot 26 and a second portion of the distal end is defined adjacent the other end of the slot.

The second strap 18 has inner and outer edges 28 and 30 respectively, both of which are serrated for most of their length. The serrations comprise a series of teeth 32, each of which has the form of an isoceles triangle (approximately a right isoceles triangle), the equal legs of the triangle forming forward and rearward tooth edges 34 and 36 respectively (FIG. 3). Tooth edges 34 and 36 may be referred to as first and second legs, respectively. The teeth are preferably equidistant, having a pitch of about three eighths of an inch. The strap 18 ends at a rounded tab 38.

As shown in FIG. 3, an imaginary line 40 colinear with the rearward edge of a tooth on one side of the second strap intersects the opposite side of the strap at a trough 42 between adjacent teeth 32. The trough-to-trough distance measured along this line (45° oblique to the length of the strap in the preferred configuration) should substantially equal or be just slightly less than the width of the slot 26, since the slot becomes aligned parallel to such a line when the visor is being worn so that said first portion of the distal end engages one of said second legs and said second portion of the distal end engages one of said first legs. (See FIGS. 2 and 3.)

In use, the wearer places the tab 38 of the second strap 18 orthogonally through the slot 26, to form a visor as shown in FIGS. 1 and 2. The natural stiffness of the bill, which is drawn from a planar shape to a conical configuration as the straps are joined, tends to rotate the second strap within the slot to an oblique alignment as shown in FIGS. 1 and 2. In this alignment, the trough-to-trough distance equals the slot length, with the teeth firmly engaging the ends of the slot, so as to provide positive locking and prevent inadvertant undoing or relaxing of the visor. Any strap tension occasioned by use increases the locking force. However, the visor can be easily readjusted or removed by grasping the end of the serrated second strap and aligning it orthogonally with the first strap so as to disengage the teeth from the ends of the slot.

The invention is subject to variations and modifications. For example, a material other than a paper product may be used, e.g., in some instances plastic may be preferred. Furthermore, the dimensions and proportions of the visor may vary, and accordingly, the foregoing should be regarded as merely illustrative of the invention defined by the following claims.

I claim:

1. A visor complaining a single blank of resilient sheet material having an arcuate bill (10) and first and second straps (16 and 18) integrally extending therefrom,
    said first strap (16) having a distal end (24) and a slot (26) extending obliquely and partially across said distal end (24) to separate said distal end into spaced first and second portions,
    said second strap (18) having a rounded tab end (38) and oppositely disposed, inner and outer serrated edges (32) defining a series of triangular teeth,
    each tooth of said series defining a generally isosceles triangle having first and second legs (34 and 36),
    said rounded tab end (38) of said second strap (18) extending through said slot (26) whereby the first and second portions of said distal end (24) are adjustably disposed on said inner and outer serrated edges (32), respectively, and said first portion engaging one of said second legs (34) and said second portion engaging one of said first legs (36), and said first portion being obliquely spaced from said second portion along an oblique line defined by said slot (26) to positively lock the first and second straps (16 and 18) together.

2. The invention of claim 1, wherein the edges of adjacent teeth intersect at troughs, and the distance between troughs on opposite sides of said second strap, as measured along a line colinear with edges of said teeth, substantially equals the width of said slot.

* * * * *